United States Patent [19]
Kato

[11] Patent Number: 5,871,360
[45] Date of Patent: Feb. 16, 1999

[54] METHOD FOR RESTORATION OF A CAVITY OF A TOOTH USING A RESIN REINFORCED TYPE GLASS IONOMER CEMENT

[75] Inventor: Shinichi Kato, Tokyo, Japan

[73] Assignee: GC Corporation, Tokyo, Japan

[21] Appl. No.: 775,415

[22] Filed: Dec. 31, 1996

[51] Int. Cl.[6] .................................. A61C 5/04; C08F 2/50
[52] U.S. Cl. ........................... 433/226; 522/908; 523/116
[58] Field of Search ................................ 433/226, 228.1; 523/116; 522/908

[56] References Cited

U.S. PATENT DOCUMENTS

| | | | |
|---|---|---|---|
| 4,648,844 | 3/1987 | Omura et al. | 433/217.1 |
| 4,696,646 | 9/1987 | Maitland | 433/149 |
| 4,738,722 | 4/1988 | Ibsen et al. | 106/35 |
| 5,063,257 | 11/1991 | Akahane et al. | 523/116 |
| 5,332,429 | 7/1994 | Mitra et al. | 106/35 |
| 5,367,002 | 11/1994 | Huang et al. | 523/116 |
| 5,453,456 | 9/1995 | Mitra et al. | 523/116 |
| 5,520,725 | 5/1996 | Kato et al. | 106/35 |
| 5,552,485 | 9/1996 | Mitra et al. | 525/102 |
| 5,670,258 | 9/1997 | Mitra et al. | 428/405 |

*Primary Examiner*—Ralph A. Lewis
*Attorney, Agent, or Firm*—Kanesaka & Takeuchi

[57] ABSTRACT

A method for restoration of a cavity of a tooth including firmly bonding a tooth and a dental composite resin by using a resin reinforced type glass ionomer cement. The method includes a step where the cavity of the tooth is treated with a tooth surface treating agent containing an aqueous solution of acid as a main component or a pre-treating agent containing an unsaturated organic compound as a main component; a step where the resin reinforced type glass ionomer cement is filled in or spread to the cavity; a step where a dental composite resin is then filled in the cavity before or after the resin reinforced type glass ionomer cement is hardened; and a step where the dental composite resin is hardened.

9 Claims, No Drawings

METHOD FOR RESTORATION OF A CAVITY OF A TOOTH USING A RESIN REINFORCED TYPE GLASS IONOMER CEMENT

BACKGROUND OF THE INVENTION AND RELATED ART STATEMENT

The present invention relates to a method for restoration of a cavity of a tooth and, more particularly, a method for restoration of a cavity of a tooth by firmly bonding a tooth and a dental composite resin with a resin reinforced type glass ionomer cement in a dental treatment for restoration of the cavity of the tooth by using the dental composite resin.

Since a dental composite resin obtained by kneading and mixing quartz powder and Bis-GMA, which is a synthesized dimethacrylate monomer was developed by R. L. Bowen in about 1960, the dental composite resin has been improved in a base monomer, filler, polymerization method or the like, and at present is widely used as a dental restorative material in view of a good aesthetic quality, reasonable cost, operational precision and the like. Further, recently, with improvement of a physical property thereof, the dental composite resin has been used as a dental restorative material to be filled into not only a anterior teeth but also a posterior teeth.

The dental composite resin is a composite material obtained by combining a methacryl resin which is an organic polymer and an inorganic and/or an organic filler. With the combination of the methacryl resin and the filler, the dental composite resin has a suitable hardness, bending strength, abrasion resistance, coefficient of thermal expansion, polymerization contraction amount, water absorption amount, or the like for use in a mouth. The dental composite resin is roughly divided into two groups, namely, a chemical polymerization type composite resin and a photo-polymerization type composite resin.

However, the dental composite resin itself does not have a bonding property with respect to a tooth. Therefore, in case the dental composite resin is filled into a cavity of a tooth, it is normally necessary to use a bonding agent to thereby adhere to the tooth. The bonding agent comprises, generally, an adhesive monomer having a hydrophobic group, such as a benzene ring and alkyl group, and a hydrophilic group, such as a phosphoric acid residual group and a carboxyl group, in the same molecule; a monomer for a purpose of a dilution or the like; a polymerization catalyst; and a solvent. The bonding agent is applied, with a sponge or the like, to a bonding surface of a tooth on which a cavity is formed, and a volatile component thereof is evaporated by air to form a thin layer thereon. If necessary, the bonding agent is hardened by chemical polymerization or photo-polymerization, and the composite resin is filled thereon to harden so that the tooth and the composite resin are bonded together.

Further, at present, there has been widely employed a tooth restorative method wherein prior to application of the bonding agent, a tooth surface treating agent containing an aqueous solution of acid as a main component and a primer containing an aqueous solution of a hydrophilic monomer or an ethanol solution as a main component are used to improve a bonding property. The tooth surface treating agent is mainly used for removing a smear layer formed by pushing against a tooth surface, saliva and cutting wastes produced when a tooth is cut or a cavity is formed. The primer is used for adapting the bonding agent to the dentin and sufficiently infiltrating the monomer of the bonding agent into the tooth. Also, the primer plays a role in reforming quality of the dentin by being applied to the dentin surface of a treated tooth and infiltrated thereto, so that the dentin is improved to be a state suitable for being bonded to the composite resin.

Therefore, a conventional tooth restorative method comprises, generally, the following steps: application of a tooth surface treating agent, washing with water and drying, application of a primer, drying, application of a bonding agent, drying and hardening, filling of a composite resin, and hardening.

However, since the conventional tooth restorative method includes many steps and is complicated, restoration of the tooth takes much time. Further, operations are very difficult, and application and drying of the primer and the bonding agent require fine techniques, so that an operational mistake is liable to occur, a big difference may be caused in finishings depending on dentists as technicians, and a stable bonding property can not be obtained. Also, in case there is a defect in bonding between the composite resin and the tooth, even in a part, water or the like penetrates through the part to cause a marginal leakage; bacteria or the like may enter therein to cause dental pulp stimulus or secondary caries, or cause marginal fracture or falling-off of the tooth.

Thus, there has been required an improved tooth restorative method wherein a treating operation can be completed in a simple method and in a short time; the composite resin and the tooth can be firmly bonded together; little difference is observed in finishings depending on technicians; and there is no possibility of pain or dental pulp stimulus after a treatment.

Therefore, it is an object of the present invention to provide a novel tooth restorative method wherein a resin reinforced type glass ionomer cement is used to firmly bond a tooth and a dental composite resin in a dental treatment for restoration of a cavity of a tooth with the dental composite resin.

SUMMARY OF THE INVENTION

A tooth restorative method, using a resin reinforced type glass ionomer cement of the invention in case of restoration of a cavity of a tooth by filling with a dental composite resin in a clinic, comprises filling or spreading the resin reinforced type glass ionomer cement to the cavity of the tooth which has been pretreated by forming the cavity by drilling or like; and filling a dental composite resin therein before or after the resin reinforced type glass ionomer cement is hardened. As a result, it is now possible that the resin reinforced type glass ionomer cement firmly bonds the dental composite resin and a tooth to thereby restore the cavity of the tooth. Thus, in comparison with a restorative method using a conventional bonding agent or the like, a dental treatment according to the method of the present invention is simple in operation, does not take a long time, has little difference in finishings depending on technicians, is safe for a living body, and does not cause any pain or a dental pulp stimulus after the treatment.

Incidentally, it is confirmed that before the resin reinforced type glass ionomer cement is filled or spread to the cavity, in case a bonding surface of the dentin is pre-treated by a tooth surface treating agent containing an aqueous solution of acid as a main component and a pre-treating agent containing an unsaturated organic compound as a main component, bonding between the tooth and the resin reinforced type glass ionomer cement is further improved.

The resin reinforced type glass ionomer cement to be used in the method of the present invention is a cement obtained by improving a conventional glass ionomer cement, wherein an unsaturated organic compound and a polymerization catalyst are added to and mixed with a fluoroaluminosilicate glass powder and a polyacrylic acid which are main components of the glass ionomer cement. Thus, the resin reinforced type glass ionomer cement has a structure such that the fluoroaluminosilicate glass powder and the polyacrylic acid cause a neutralization reaction and a polymerization reaction of the unsaturated organic compound takes place due to a photo-polymerization or chemical polymerization to thereby harden. As the unsaturated organic compound, there is a polymerizable unsaturated organic compound having at least one of $CH2=C(R1)-COO-$ (wherein R1 is H or CH3), such as an acrylic ester or methacrylic ester which are exemplified in U.S. Pat. No. 5,063,257. Also, as the polymerization catalyst, there are a chemical polymerization catalyst and photo-polymerization catalyst of a known redox polymerization system, wherein an organic peroxide, such as benzoyl peroxide; a photo-polymerization initiator, such as camphorquinone; and an amine compound, such as dimethyl-p-toluidine are combined.

The resin reinforced type glass ionomer cement overcomes defects, such as weakening, breaking and cloudiness, caused by contact with water at an early stage of hardening of the conventional glass ionomer cement. Also, the resin reinforced type glass ionomer cement has excellent physical properties improved in an initial hardness, bonding strength with a tooth, bending strength, transparency and the like. Representative products of this type of cement are "FUJI II LC", "FUJI BOND LC" and "FUJI DUET" (manufactured by GC Corporation); "Photac-fil" (manufactured by ESPE Fabrik Pharmazeutischere Präparate GmbH); "Vitremer" and "Vitrebond" (manufactured by 3M Company). Further, as the resin reinforced type glass ionomer cement, there are various types of combinations, such as a powder and a liquid; a paste and a liquid; and a paste and a paste, and any type of the resin reinforced type glass ionomer cement can be used.

As one of typical characteristics, the resin reinforced type glass ionomer cement has a chemical bonding property with respect to the tooth and the dental composite resin. It is said that the bonding property of the resin reinforced type glass ionomer cement with respect to the tooth is caused by a chelate bond, hydrogen bond or ion bond between a carboxylic group in a cement mixture and a hydroxyl group, a calcium ion, hydrogen ion, a carboxyl group of collagen which is organic, or an amino group, of an apatite surface layer of the tooth. On the other hand, the bonding property of the resin reinforced type glass ionomer cement with respect to the dental composite resin is supposed to be caused by a covalent bond taking place between the composite resin and the resin reinforced type glass ionomer cement.

Incidentally, as the tooth surface treating agent containing the aqueous solution of acid as a main component for treating a tooth bonding surface before the resin reinforced type glass ionomer cement is filled therein or spread thereto, there is a tooth surface treating agent containing an aqueous solution of acid as a main component of a polymer of an inorganic acid, such as phosphoric acid, hydrochloric acid and nitric acid; an organic acid, such as oxalic acid, citric acid, formic acid, acetic acid, tartaric acid, maleic acid, fumaric acid, acrylic acid and methacrylic acid; and an unsaturated organic acid, such as polyacrylic acid, polymaleic acid and polymethacrylic acid. Also, there can be used a tooth surface treating agent wherein a metallic salt of iron, aluminum, tin or calcium is added to the above described tooth surface treating agent.

Also, as a pre-treating agent containing an unsaturated organic compound for treating the tooth bonding surface before the resin reinforced type glass ionomer cement is filled therein or spread thereto, there is a pre-treating agent wherein a polymerizable unsaturated organic compound containing at least one of $CH2=C(R1)-COO$ (wherein R1 is H or CH3), such as the same kind of an acrylic ester or a methacrylic ester as the unsaturated organic compound added to and mixed with the resin reinforced type glass ionomer cement, is dissolved in water and organic solvent, such as ethanol or acetone as a solvent. Further, there is a pre-treating agent wherein in the above obtained pre-treating agent are dissolved a chemical polymerization catalyst and a photo-polymerization catalyst of the known redox polymerization system represented by a combination of an organic peroxide, such as benzoylperoxide, which is a polymerization catalyst and an amine compound; and a combination of a photo-polymerization initiator, such as camphorquinone, and an amine compound. It is believed that in case the tooth bonding surface is pre-treated with the tooth surface treating agent and the pre-treating agent as described above, the chelate bond, hydrogen bond and ion bond caused between the tooth and the resin reinforced type glass ionomer cement are further strengthened to thereby improve the bonding property therebetween.

Also, in the method of the present invention, it is possible to use the known chemical polymerization type or photo-polymerization type dental composite resin which has been conventionally used for restoration of a tooth. Further, there are a dental composite resin of one paste type and a dental composite resin of two paste type, and both of them are usable in the present invention.

The present invention is a tooth restoring method taking advantage of a property wherein the resin reinforced type glass ionomer cement chemically adheres to the tooth and the dental composite resin. Hereinafter, the tooth restoring method of the invention using the resin reinforced type glass ionomer cement is explained in detail according to restoring procedures.

1. First, the resin reinforced type glass ionomer cement in a mixed non-hardened state is filled into or spread to an inner wall of a tooth on which a cavity is formed. Normally, the resin reinforced type glass ionomer cement is filled into the cavity with a certain thickness. However, in case the resin reinforced type glass ionomer cement has a high fluidity, it is spread to a cavity wall.

2. Next, the dental composite resin is filled thereinto. At this time point, the resin reinforced type glass ionomer cement may be either hardened or not hardened. However, in case the photo-polymerization resin reinforced type glass ionomer cement is used, it is preferable that the resin reinforced type glass ionomer cement is hardened. The resin reinforced type glass ionomer cement causes the hydrogen bond and ion bond with dentin components in a hardening stage to thereby chemically adhere thereto. In case the resin is filled after the resin reinforced type glass ionomer cement is hardened, the resin reinforced type glass ionomer cement is hardened by the chemical polymerization or photo-polymerization which is a hardening reaction of the cement itself.

3. Next, the dental composite resin is hardened to thereby complete a restoring work. Incidentally, the dental composite resin is hardened according to a polymerization method of the composite resin itself. In case the photo-polymerization type resin reinforced type glass ionomer cement and the photo-polymerization type composite resin are employed together, since the composite resin itself has a certain light translucency, the photo-polymerization type glass ionomer cement in the non-hardened state which is filled or spread beforehand can be hardened at the same time by light irradiation for polymerizing the composite resin.

The tooth restoring method of the invention using the resin reinforced type glass ionomer cement basically comprises very few steps: filling or spreading the resin reinforced type glass ionomer cement, filling with the composite resin and then hardening. Therefore, even if the pre-treating operation is carried out, the tooth restoring operation of the present invention is simpler and takes a shorter time in comparison with the conventional tooth restoring method. Further, there is little difference in finishings depending on technicians.

Also, in the present invention, since the resin reinforced type glass ionomer cement having a good biocompatibility affinity is used, the present method is safer for a vital body; there is no pain and dental pulp irritation after the treatment in comparison with a method using a conventional bonding agent and the like. Further, due to a fluoride releasing property of the glass ionomer cement, it is anticipated that the present method strengthens the tooth and prevents caries of teeth.

Incidentally, the method of the present invention includes a restoring method by filling the resin reinforced type glass ionomer cement and the dental composite resin in a laminated state. In this case, the above described steps 1–3, i.e., the resin reinforced type glass ionomer cement is filled or spread; the dental composite resin is filled; and the dental composite resin is hardened, are repeated. Especially, in case of a deep cavity in a molar portion, by forming a layer of the resin reinforced type glass ionomer cement between the composite resin and the composite resin with lamination fillings, the present method is suitable for a case where it is anticipated that a bonding strength is improved and stress is relieved.

Further, the method of the invention includes a step where a bonding portion of a tooth is pre-treated before the resin reinforced type glass ionomer cement is filled or spread. In this step, the bonding surface of the tooth prior to filling or spreading of the resin reinforced type glass ionomer cement is pre-treated with a tooth surface treating agent containing an aqueous solution of acid as a main component to remove a smear layer produced due to cutting wastes of the tooth when the cavity is formed; or the bonding surface of the tooth is pre-treated with a pre-treating agent containing an unsaturated organic compound as a main component to thereby provide a chemical bonding property. Thus, bonding between the tooth and the resin reinforced type glass ionomer cement can be further strengthened and made more stable.

EXAMPLES

Next, a method for restore a cavity of a tooth using a resin reinforced type glass ionomer cement of the present invention is specifically described with an embodiment. Although, in the present embodiment, the resin reinforced type glass ionomer cement described hereunder was prepared and used, the resin reinforced type glass ionomer cement is not limited to the present embodiment.

Preparation of a Photo-polymerization Type Resin Reinforced Type Glass Ionomer Cement 23 g of aluminum oxide, 41 g of silicic acid anhydride, 10 g of strontium fluoride, 13 g of aluminum phosphate and 13 g of calcium phosphate were well mixed and dissolved in a high-temperature electric furnace at 1,100° C. After dissolving, the mixture was cooled and crushed in a ball mill to obtain a powder passed through 200 mesh (ASTM) sieve.

20 g of an ethanol solution of 10% vinyl triethoxysilane was added to 100 g of the thus obtained powder for subjecting to a silane treatment. 1 g of benzenesulfohydroxamic acid, 1 g of tin fluoride and 1 g of benzyl dimethylketal were added to and mixed with 100 g of the thus silane-treated powder to prepare a cement powder.

On the one hand, 30 g of polyacrylic acid having an average molecular weight of 20,000, 10 g of di-2-methacryloxyethyl-hexamethylenedicarbamate, 15 g of neopentylglycoldiacrylate, 44 g of distilled water and 1.0 g of camphorquinone were stirred and mixed to be uniform to thereby prepare a cement liquid.

Preparation of a Chemical Polymerization Type Resin Reinforced Type Glass Ionomer Cement 25 g of aluminum oxide, 40 g of silicic acid anhydride, 12 g of strontium fluoride, 10 g of aluminum phosphate and 13 g of calcium phosphate were well mixed and dissolved in a high-temperature electric furnace at 1,100° C. After dissolving, the mixture was cooled and crushed in a ball mill to obtain a powder passed through 200 mesh (ASTM) sieve. 20 g of an ethanol solution of 10% vinyl triethoxysilane was added to 100 g of the thus obtained powder for subjecting to a silane treatment. 1 g of benzenesulfohydroxamic acid and 1 g of tin fluoride were added to and mixed with 100 g of the thus silane-treated powder to prepare a cement powder.

On the one hand, 30 g of polyacrylic acid having an average molecular weight of 30,000, 10 g of di-2-methacryloxyethyl-hexamethylenedicarbamate, 15 g of neopentylglycoldiacrylate and 45 g of distilled water were stirred and mixed to be uniform to thereby prepare a cement liquid.

Example 1

A class-V cavity, having a diameter of about 3 mm and a depth of about 1 mm, of a crown portion of a left central incisor on an upper jaw was washed with water and dried. Then, the photo-polymerization type resin reinforced type glass ionomer cement prepared by mixing the powder and liquid at a rate of 2:1 was filled into the class-V cavity and irradiated with light for 20 seconds to harden; a dental composite resin (manufactured by 3M Company, under the trademark "Z-100") was filled thereto and irradiated with light for 40 seconds to thereby harden. Thereafter, a finish polishing was carried out to complete a treatment of the tooth. Progress after the treatment was good. Even six months later, marginal fracture, marginal discoloration, secondary caries and pain after the treatment were not observed.

Example 2

A class-V cavity, having a diameter of about 3 mm and a depth of about 1 mm, of a crown portion of a left central incisor on an upper jaw was washed with water and dried. Then, the chemical polymerization type resin reinforced type glass ionomer cement prepared by mixing the powder and liquid at a rate of 2:1 was filled into the class-V cavity; a dental composite resin (manufactured by 3M Company, under the trademark "Z-100") was filled thereto before the resin reinforced type glass ionomer cement was hardened and irradiated with light for 40 seconds to thereby harden. Thereafter, a finish polishing was carried out to complete a treatment of the tooth. Progress after the treatment was good. Even six months later, a marginal fracture, marginal discoloration, secondary caries and pain after the treatment were not observed.

Example 3

A class-V cavity, having a diameter of about 3 mm and a depth of about 1 mm, of a crown portion of a right central incisor on a lower jaw was washed with water and dried. Then, the photo-polymerization type resin reinforced type glass ionomer cement prepared by mixing the powder and liquid at a rate of 0.7:1 was applied to the class-V cavity with a brush; light was irradiated to the cavity surface for 20 seconds to harden; a dental composite resin (manufactured by 3M Company, under the trademark "Z-100") was filled into the cavity and irradiated with light for 40 seconds to thereby harden. Thereafter, a finish polishing was carried out to complete a treatment of the tooth. Progress after the treatment was good. Even six months later, a marginal fracture, marginal discoloration, secondary caries and pain after the treatment were not observed.

Example 4

A class-V cavity, having a diameter of about 3 mm and a depth of about 1 mm, of a crown portion of a right canine on an upper jaw was washed with water and dried. After a tooth surface treating agent (manufactured by GC Corporation, under the trademark "DENTIN CONDITIONER") was applied to the cavity and left for 20 seconds, the cavity was washed with water and dried. Then, after the photo-polymerization type resin reinforced glass ionomer cement prepared by mixing the powder and liquid at a rate of 2:1 was filled into the cavity, a dental composite resin (manufactured by 3M Company, under the trademark "Z-100") was filled into the cavity and irradiated with light for 60 seconds to harden the resin reinforced type glass ionomer cement and the composite resin at the same time. Thereafter, a finish polishing was carried out to complete a treatment of the tooth. Progress after the treatment was good. Even six months later, a marginal fracture, marginal discoloration, secondary caries and pain after the treatment were not observed.

Example 5

A class-V cavity, having a diameter of about 3 mm and a depth of about 1 mm, of a crown portion of a right canine on an upper jaw was washed with water and dried. After a tooth surface treating agent (manufactured by GC Corporation, under the trademark "DENTIN CONDITIONER") was applied to the cavity and left for 20 seconds, the cavity was washed with water and dried. Then, after the chemical polymerization type resin reinforced type glass ionomer cement prepared by mixing the powder and liquid at a rate of 2:1 was filled into the cavity and hardened, a dental composite resin (manufactured by 3M Company, trade name "Z-100") was filled into the cavity and irradiated with light for 40 seconds to harden. Thereafter, a finish polishing was carried out to complete a treatment of the tooth. Progress after the treatment was good. Even six months later, a marginal fracture, marginal discoloration, secondary caries and pain after the treatment were not observed.

Example 6

An class-I cavity, having a diameter of about 4 mm and a depth of about 3 mm, of a biting surface portion of a right first molar on a lower jaw was washed with water and dried. Next, after a tooth surface treating agent (manufactured by GC Corporation, under the trademark "DENTIN CONDITIONER") was applied to the cavity and left for 20 seconds, the cavity was washed with water and dried. Then, after the photo-polymerization type resin reinforced type glass ionomer cement prepared by mixing the powder and liquid at a rate of 0.7:1 was applied to the cavity by a brush and irradiated with light for 20 seconds to harden, a dental composite resin (manufactured by 3M Company, under the trademark "Z-100") was filled up to a depth of about 2 mm of the cavity and irradiated with light for 40 seconds to harden. Thereafter, again, after the resin reinforced type glass ionomer cement prepared by mixing a powder and liquid at a rate of 0.7:1 was applied to the cavity by a brush and irradiated with light for 20 seconds to harden, the dental composite resin (manufactured by 3M Company, under the trademark "Z-100") was filled and irradiated with light for 40 seconds to harden. Thereafter, a finish polishing was carried out to complete a treatment of the tooth. Progress after the treatment was good. Even six months later, a marginal fracture, marginal discoloration, secondary caries and pain after the treatment were not observed.

Comparison Example 1

A class-V cavity, having a diameter of about 3 mm and a depth of about 1 mm, of a crown portion of a left central incisor on an upper jaw was washed with water and dried. Then, the cavity was pre-treated (tooth surface treatment for 15 seconds—washing with water, drying—primer application—drying—bonding agent application—light irradiation for 10 seconds) with a bonding agent for a dental composite resin (manufactured by 3M Company, under the trademark "SCOTCHBOND MULTI-PURPOSE SYSTEM") sold on the market. Then, the dental composite resin (manufactured by 3M Company, under the trademark "Z-100") was filled into the cavity and irradiated with light for 40 seconds to harden. Thereafter, a finish polishing was carried out to complete a treatment of the tooth. The treatment with the bonding agent was very complicated and took a long time. Progress after the treatment was good. Even six months later, a marginal fracture, marginal discoloration, secondary caries and pain after the treatment were not observed.

Comparison Example 2

A class-V cavity, having a diameter of about 3 mm and a depth of about 1 mm, of a crown portion of a right central incisor on a lower jaw was washed with water and dried. Then, the cavity was pre-treated (tooth surface treatment for 15 seconds—washing with water, drying—kneading and mixing of primers A, B—primer application—drying—bonding agent application—light irradiation for 20 seconds) with a bonding agent for a dental composite resin (manufactured by Bisco Co., under the trademark "ALL BOND 2 SYSTEMS") sold on the market. Then, the dental composite resin (manufactured by 3M Company, under the trademark "Z-100") was filled into the cavity and irradiated with light for 40 seconds to harden. Thereafter, a finish polishing was carried out to complete a treatment of the tooth. The treatment with the bonding agent was very complicated and took a long time. A progress after the treatment was approximately good. Even six months later, a marginal fracture, secondary caries and pain after the treatment were not observed. However, marginal discoloration was observed on a part of the treated portion.

As described in detail, the present invention is to provide a method for restore a cavity of a tooth by a simple operation, wherein the resin reinforced type glass ionomer cement is filled in or spread to the cavity of the tooth, and the dental composite resin is filled thereon to harden. The resin reinforced type glass ionomer cement of the invention provides a firm bonding between the composite resin and a tooth. Therefore, in comparison with a restoring method using a conventional bonding agent and the like, according to the method of the present invention, operations are simple, a time taken for restoring the tooth can be shortened, there is little difference in finishings depending on technicians, the method is safe for a vital body and there is no possibility of pain and a dental pulp irritation after treatments. Further, due to fluoride releasing property of the resin reinforced type glass ionomer cement, it is anticipated from the present method to strengthen a tooth and prevent caries of teeth.

What is claimed is:

1. A tooth restorative method using a resin reinforced type glass ionomer cement in a dental treatment for filling a cavity of a tooth with a dental composite resin, comprising:

treating the cavity of the tooth by a tooth surface treating agent containing as a main component an acid solution and a metallic salt;

providing said resin reinforced type glass ionomer cement to the cavity of the tooth;

filling said dental composite resin thereto before or after said resin reinforced type glass ionomer cement is hardened; and hardening said dental composite resin.

2. A tooth restorative method using a resin reinforced type glass ionomer cement according to claim 1, wherein said resin reinforced type glass ionomer cement contains a fluoroaluminosilicate glass powder, polycarboxylic acid, unsaturated organic compound and polymerization catalyst as components.

3. A tooth restorative method using a resin reinforced type glass ionomer cement according to claim 1, wherein said acid solution contains an acid selected from the group consisting of phosphoric acid, hydrochloric acid, nitric acid, oxalic acid, citric acid, formic acid, acetic acid, tartaric acid, maleic acid, fumaric acid, acrylic acid, methacrylic acid, polyacrylic acid, polymaleic acid and polymethacrylic acid.

4. A tooth restorative method using a resin reinforced type glass ionomer cement according to claim 3, wherein said metallic salt contains metal selected from the group consisting of iron, aluminum, tin and calcium.

5. A tooth restorative method using a resin reinforced type glass ionomer cement according to claim 3, wherein said acid solution contains a polyacrylic acid, and said metallic salt contains metal selected from the group consisting of iron, aluminum, tin and calcium.

6. A tooth restorative method using a resin reinforced type glass ionomer cement in a dental treatment for filling a cavity of a tooth with a dental composite resin, comprising:

treating the cavity of the tooth by a tooth surface treating agent including a polymerizable unsaturated organic compound containing at least one radical of $CH_2 = C(R_1)-COO$ wherein $R_1$ is H or $CH_3$, and a solvent for dissolving the polymerizable unsaturated organic compound;

providing said reinforced type glass ionomer cement to the cavity of the tooth;

filling said dental composite resin thereto before or after said resin reinforced type glass ionomer cement is hardened; and hardening said dental composite resin.

7. A tooth restorative method using a resin reinforced type glass ionomer cement according to claim 6, wherein said solvent is selected from the group consisting of water, ethanol and acetone.

8. A tooth restorative method using a resin reinforced type glass ionomer cement according to claim 7, wherein said tooth surface treating agent further includes a chemical polymerization catalyst of a redox polymerization system containing an organic peroxide and an amine compound.

9. A tooth restorative method using a resin reinforced type glass ionomer cement according to claim 7, wherein said tooth surface treating agent further includes a photo-polymerization catalyst containing a photo-polymerization initiator and an amine compound.

* * * * *